United States Patent [19]

Parlenvi et al.

[11] 4,421,488
[45] Dec. 20, 1983

[54] AID FOR CURING OR MITIGATING STAMMERING

[76] Inventors: Paul Parlenvi, Perhans Vag 11A, Hovas (S-4308); Ingemar H. G. Almslätt, Skattkarr 2, S 43370 Partille, both of Sweden

[21] Appl. No.: 321,170
[22] PCT Filed: Mar. 3, 1981
[86] PCT No.: PCT/SE81/00057
 § 371 Date: Nov. 6, 1981
 § 102(e) Date: Nov. 6, 1981
[87] PCT Pub. No.: WO81/02513
 PCT Pub. Date: Sep. 17, 1981

[30] Foreign Application Priority Data
Mar. 10, 1980 [SE] Sweden .............................. 8001848

[51] Int. Cl.³ .............................................. G09B 5/04
[52] U.S. Cl. ........................................ 434/185; 381/1
[58] Field of Search ........... 434/185; 179/1 G, 107 R, 179/107 FD; 128/1 R

[56] References Cited

U.S. PATENT DOCUMENTS

| | | | |
|---|---|---|---|
| 3,101,081 | 8/1963 | Tomatis | 128/1 R |
| 3,349,179 | 10/1967 | Klein | 128/1 R X |
| 3,504,120 | 3/1970 | Levitt | 179/1 G |
| 3,566,858 | 3/1971 | Larson et al. | 434/185 X |
| 3,773,032 | 11/1973 | Donovan et al. | 434/185 X |
| 3,894,196 | 7/1975 | Briskey | 179/107 FD |

FOREIGN PATENT DOCUMENTS 2260153  8/1975  France .............................. 434/185

OTHER PUBLICATIONS

Biomedical Engineering, Dec. 1976, pp. 413, 414 and Title Page.

*Primary Examiner*—William H. Grieb

[57] ABSTRACT

An aid for curing or mitigating stammering comprises two earphones and at least one microphone which are connected with an amplifier, and a delay unit in which the signal from the amplifier to one earphone is delayed in relation to the signal which is transmitted to the other earphone.

5 Claims, 1 Drawing Figure

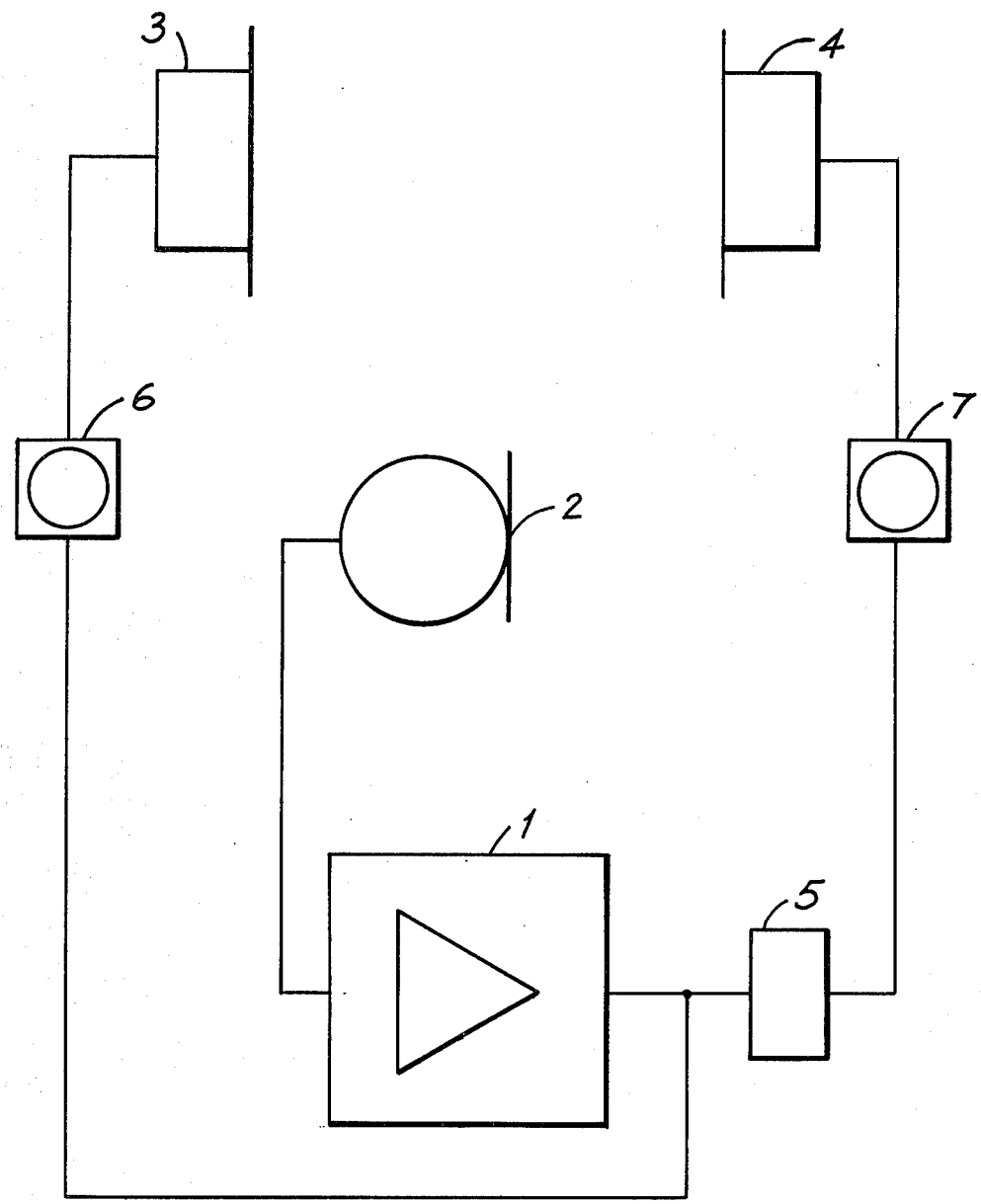

AID FOR CURING OR MITIGATING STAMMERING

The present invention relates to an aid for curing or mitigating stammering.

It is a principal object of the present invention to provide an aid of the kind mentioned above, which is effective at the same time as it is simple, as it is comprised of few components and is simple to use.

Said object is obtained by means of an aid according to the present invention, which is substantially characterized by two ear phones and at least one microphone being connected with an amplifier, the aid also having a delaying unit, in which the signal from the amplifier to one of the ear phones is delayed relative to the signal which is transmitted to the other ear phone.

The invention is described in the following, reference being made to the accompanying drawing illustrating a schematic coupling diagram for the components forming part of the aid.

An amplifier 1 is by way of example via circuits connected on the one hand with a microphone 2 and on the other with two earphones 3, 4. If the aid is intended for use as a stationary device, the earphones 3, 4 can comprise connections to head phones, and if the aid is intended for portable use, they can comprise miniature earphones of the type that can be inserted into the auditory canal. The earphones 3, 4 and the microphone 2 can also be coupled together to form a portable unit.

A delaying unit 5, which is either assembled with the amplifier 1 or, as is shown in the wiring diagram, cut in after the output for the signal to one earphone 3, is arranged to delay the signal from the amplifier 1 to the other earphone 4 in relation to the signal which is transmitted to the first earphone 3. This delaying unit 5 can also have means for adjustment, by means of which the time delay between the two signals can be adjusted. The delay of the signal to the earphone 4 relative to the earphone 3 can by way of example be adjusted from a hardly noticeable interval up to one of approximately one second. Two volume controls for each earphone 3 and 4 respectively are in the drawing indicated with 6 and 7 respectively, and a desired volume can by means of these volume controls be adjusted for each one of the earphones independent of each other.

Also the amplifier 1 and the delay unit 5 as to their size can be designed in such a manner that the whole aid will be easy to use and portable.

The function of the aid described above will now be described more in detail. Depending upon whether the individual has his motory center for speech in his right or in his left cerebral hemisphere, the earphones 3, 4 are put on in such a manner that a right-handed person gets the earphone 4, which is designed to transmit a delayed signal, coupled to his left ear and the reverse for a left-handed person. The speech of the user himself as well as the speech of other people and other sound is recorded by the microphone 2 and is transmitted to the amplifier 1. The recorded sound signal is transmitted to the right ear of the right-handed person by means of the earphone 3, which has no delay possibility, so that the information substantially is transmitted to said ear without delay, when the sound signal, which is transmitted to the earphone 4 of the left ear, is delayed, as this signal first passes through the delaying unit 5.

The sound level is subsequently adjusted by means of the sound level controls 6, 7, of which the one indicated with 6 belongs to the earphone 3, the other one belonging to the earphone 4. In this connection one has to see to it that the sound level for the earphone 4 provided with a delaying possibility is suitably somewhat higher than the sound level for the earphone 3. By means of the adjusting device for the delaying unit 5, a suitable time-delay is thereafter adjusted for the earphone 4 in relation to the earphone 3. In cases of severe stammering a longer-time delay is adjusted than when there is only a slight stammering.

When the aid is in use, one cerebral hemisphere does not have time to transmit and disturb the thoughts and information to the vocal chords etc. of the first mentioned cerebral hemisphere, whereby a stammering is avoided or minimized. As already mentioned the earphones are for a left-handed person connected in the reverse order, the same result with respect to the stammering being obtained.

The aid is intended to be used either as a stationary instrument or as a portable device to be brought along by the user depending upon age and intensity of the stammering.

The invention is not limited to the example of embodiment described above and illustrated in the drawing, but can be varied within the scope of the following claims.

We claim:

1. A device for curing or mitigating stammering of a person, comprising: at least one microphone, an amplifier operatively connected to said microphone, two earphones operatively connected to said amplifier, and a delay unit in the connection between said amplifier and one of said earphones for delaying a signal from the amplifier to said one earphone in relation to the signal from the amplifier to the other earphone so that the signal transmitted without delay to one ear of the person via said other earphone is perceived faster to the dominating cerebral hemisphere of the person than to the other cerebral hemisphere to thereby at least mitigate stammering.

2. A device according to claim 1, wherein said earphones and said microphone are coupled together to form a portable unit.

3. A device according to claim 1 or 2, wherein said delay unit has an adjusting device, by means of which the time delay between the signals is adjustable.

4. A device according to claim 1 or 2, wherein said delay unit is assembled together with the amplifier to form a portable unit.

5. A device according to claim 1 or 2, wherein said two earphones have controls for individual adjustment of the volume of the respective earphone.

* * * * *